(12) United States Patent  
Pansiera et al.

(10) Patent No.: US 8,123,711 B2  
(45) Date of Patent: Feb. 28, 2012

(54) SNAP LOCK ASSISTED MECHANICAL JOINT

(75) Inventors: Timothy T. Pansiera, Weaverville, NC (US); David Lee Stubbers, Bradenton, FL (US)

(73) Assignee: Fillauer Companies, Inc., Chattanooga, TN (US)

( * ) Notice: Subject to any disclaimer, the term of this patent is extended or adjusted under 35 U.S.C. 154(b) by 446 days.

(21) Appl. No.: 12/507,773

(22) Filed: Jul. 22, 2009

(65) Prior Publication Data

US 2010/0022929 A1    Jan. 28, 2010

Related U.S. Application Data

(60) Provisional application No. 61/083,516, filed on Jul. 24, 2008.

(51) Int. Cl.  
*A61F 5/00* (2006.01)

(52) U.S. Cl. .................. 602/16; 602/5; 602/20; 602/23; 602/26; 74/411.5

(58) Field of Classification Search ................ 602/5, 12, 602/16, 23, 26; 128/878, 881, 882; 482/118–119; 74/411.5, 575–578; 16/354; 623/45; 297/362, 297/366  
See application file for complete search history.

(56) References Cited

U.S. PATENT DOCUMENTS

| | | | | |
|---|---|---|---|---|
| 2,943,622 A * | 7/1960 | Nelson | ............................. | 602/16 |
| 4,433,679 A * | 2/1984 | Mauldin et al. | ................. | 602/16 |
| 4,502,472 A * | 3/1985 | Pansiera | ........................... | 602/16 |
| 4,520,804 A * | 6/1985 | DiGeorge | ........................ | 602/16 |
| 4,738,252 A * | 4/1988 | Friddle et al. | .................... | 602/16 |
| 5,437,619 A * | 8/1995 | Malewicz et al. | ................ | 602/16 |
| 5,759,165 A * | 6/1998 | Malewicz | ........................ | 602/21 |
| 5,776,086 A * | 7/1998 | Pansiera | ........................... | 602/16 |
| 5,860,943 A * | 1/1999 | Bloedau et al. | .................. | 602/16 |
| 5,899,869 A * | 5/1999 | Barrack et al. | ................... | 602/16 |
| 6,517,503 B1 * | 2/2003 | Naft et al. | ........................ | 602/16 |
| 6,598,724 B1 * | 7/2003 | Stedman et al. | ............... | 192/217 |
| 6,764,244 B2 * | 7/2004 | Pansiera | ........................ | 403/102 |
| 6,960,175 B1 * | 11/2005 | Myers | .............................. | 602/16 |
| 7,156,818 B2 * | 1/2007 | Salmon et al. | ..................... | 602/5 |
| 7,462,159 B1 * | 12/2008 | Shlomovitz et al. | ............ | 602/16 |
| 7,662,118 B2 * | 2/2010 | Pansiera | ........................... | 602/16 |
| 2005/0273025 A1 * | 12/2005 | Houser | ............................ | 602/16 |
| 2010/0160844 A1 * | 6/2010 | Gilbert et al. | .................... | 602/16 |

* cited by examiner

*Primary Examiner* — Patricia Bianco  
*Assistant Examiner* — Kari Petrik  
(74) *Attorney, Agent, or Firm* — Chambliss, Bahner & Stophel, P.C.

(57) ABSTRACT

A compact close contour mechanical joint that uses a snap ring, a transfer gear partially press-fit into a brake wheel, a distal bar having integral gear teeth that engage the exposed portion of the transfer gear, a second bar with a T-shaped proximal end, a handle disengaging an unlocking pin to separates gear teeth that allows incremental distal bar movement, and a two-axis arrangement for distal bar rotation. Instead of using a spring biasing member, the mechanical joint uses a gear ratio reduction that provides a smaller stop increment, less travel, enhanced joint strength, less stress on gear teeth, and less force required to unlock it than prior close contour joints. Although it is contemplated for use of the mechanical joint to be primarily in orthotic, any application for which the mechanical joint's compact configuration would provide some assistance or technical advantage is considered to be within its scope.

19 Claims, 8 Drawing Sheets

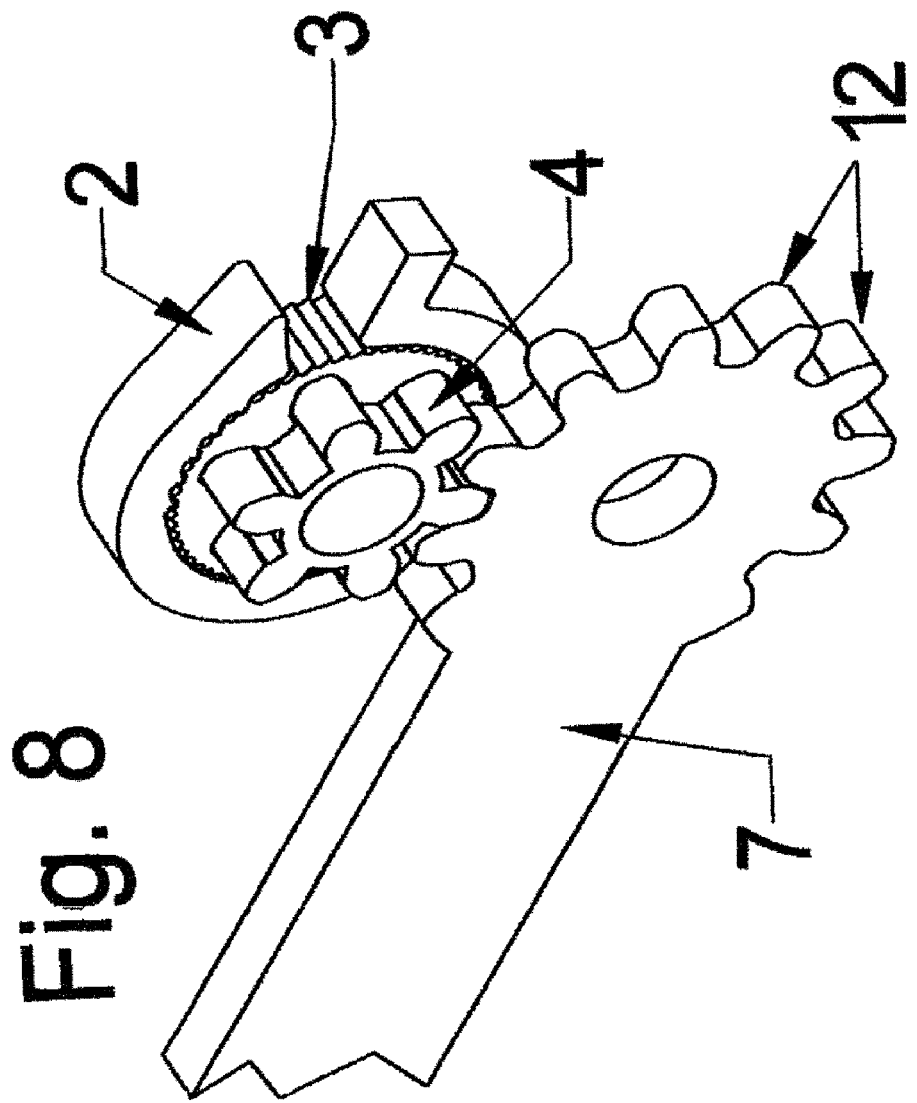

SNAP LOCK ASSISTED MECHANICAL JOINT

CROSS-REFERENCES TO RELATED APPLICATIONS

The applicants claim domestic benefit for their U.S. provisional patent application having the Ser. No. 61/083,516, which was filed on Jul. 24, 2008, with the title of "Snap Lock Assisted Mechanical Joint". Thus, all benefit to which the applicants are entitled as a result of their previously-filed provisional patent application referenced immediately hereinabove, is hereby requested.

BACKGROUND

1. Field of the Invention

This invention relates to the field of mechanical joints for use in orthotic and prosthetic devices, specifically to an improved close contour mechanical joint primarily contemplated for orthotic use to assist the movement of an inadequately functioning body limb, the benefits of which include but are not limited to a compact configuration, enhanced joint strength, enhanced operational efficiency, decreased stress and wear on moving components, and enhanced user comfort and security. It comprises a distal bar having a large gear configuration integral to its proximal end and an opposed end that is configured for connection to orthotic hardware secured to the lower portion of a body limb, as well as a proximal bar (also referred to herein as a T-bar) having a T-shaped proximal end and an opposed end that is configured for connection to orthotic hardware secured to the upper portion of a body limb. For movement of the distal bar relative to the T-bar between positions of complete flexion and full extension (approximately the full 135-degree range of anatomical motion), the present invention also uses a snap ring, a brake wheel, and a transfer gear as part of its improved interior design. Therefore, instead of using a spring biasing member, as in prior close contour orthotic joints, the snap ring, brake wheel, and transfer gear (part of which is press-fit into a central area in the brake wheel), in combination with a gear configuration integral to the proximal end of the distal bar, produce a gear ratio reduction (preferably 2:1 in many orthotic applications) that allows a smaller stop increment for distal bar movement (approximately three degrees), less travel for each stop increment, less stress on gear teeth, and enhanced joint strength. In addition, as a result of its design improvements, less force is required to unlock the present invention close contour mechanical joint than is typically required for many currently used close contour joints for enhanced user convenience, and the T-bar is secured within a T-shaped recess in the joint's protective housing (hereinafter also referred to as the "main body") for enhanced joint strength and compactness. When the present invention mechanical joint is in its fully extended orientation, the T-bar extends from the main body in a direction substantially opposite to that of the distal bar. Furthermore, a two-axis (co-linear) construction that further enhances joint strength and compactness is used for distal bar and T-bar connection to the main body, and in addition, the snap ring positioned around the present invention brake wheel (and having ratchet teeth that engage a pawl surface on the exterior of the brake wheel) is progressively moved into an opened position by a user employing a conveniently accessed handle connected to an unlocking pin having non-symmetrical perimeter configuration, with the opened snap ring position allowing free movement of the brake wheel (and thus free distal bar movement relative to the T-bar), and also with further rotation of the unlocking pin moving the snap ring again into it closed position wherein its ratchet teeth re-engage the brake wheel's pawl surface to provide one-direction brake wheel movement with incremental stops (and thus distal bar movement in the direction of maximum extension with a very small stop increment reduced by the gear ratio reduction of the transfer gear and the large gear configuration integral to the distal bar's proximal end). Although it is contemplated for use of the present invention to be primarily in orthotic devices, and particularly in orthotic devices used for infants and children, application in any device needing a mechanical joint for which the compact configuration and/or strength of the present invention would provide some assistance or technical advantage is considered to be within the scope of the present invention.

2. Description of the Related Art

Components used in orthotic devices and prosthetic devices should be compact and minimally intrusive for ease of use, enhanced social acceptability, and a lessened risk of hazard or damage during use. Further, a user should not experience insecurity, discomfort, or apprehension as a result of any aspect of their performance. As a fundamental part of their construction, all mechanical joints used in orthotic devices must include design features and/or apparatus that define the limits of their flexion and extension, and movement provided therebetween should avoid excesses and insufficiencies of motion. Often, mechanical joints are bulky in configuration, provide an abrupt stop for the user, and/or fail to provide proper support for a user when the joint nears maximum extension. Orthotic devices should also be as simple as possible for ease of manufacture and convenience during their function. The use of a snap ring, a brake wheel, and a transfer gear to provide improved interior design is new in the field of close contour orthotic joints. Instead of using a spring biasing member, as in many prior and currently used close contour orthotic joints, the snap ring, brake wheel, and transfer gear (part of which is press-fit into the brake wheel), in combination with a gear configuration integral to the proximal end of the distal bar, produce a reducing gear ratio (preferably 2:1 or close thereto) that allows a smaller stop increment, less travel, less stress and wear on gear teeth, and enhanced joint strength. In addition, less force is required to unlock it than is typically required for prior close contour joints. Furthermore, the distal bar and the T-shaped bar are pivotally connected to one another using a two axis (co-linear) construction that provides further compactness and operational efficiency in the present invention close contour mechanical joint. No other mechanical joint is known to have the same structure, function in the same manner, or provide all of the advantages of the present invention.

BRIEF SUMMARY OF THE INVENTION

The primary object of this invention to provide a mechanical joint for an orthotic device with a smaller stop increment, less travel, enhanced joint strength, and less force required to unlock it than currently used close contour joints. Another object of this invention is to provide a mechanical joint for an orthotic device with controlled motion in both the extension and flexion directions. It is a further object of this invention to provide a mechanical joint for an orthotic device that has pediatric applications. Another object of this invention is to provide a mechanical joint for an orthotic device that is easily locked and unlocked. It is a further object of this invention to provide a mechanical joint for an orthotic device that is simple and cost-effective to assemble and manufacture. It is also an object of this invention to provide a mechanical joint for an orthotic device that functions unobtrusively and with cosmetic advantage.

The present invention, when properly made and used, will provide a close contour mechanical joint that is particularly effective in pediatric orthotic applications, but also effective for other orthotic applications as well, to assist the movement of an inadequately functioning body limb. However, although orthotic applications are important to the present invention, it can also be used in any other application where substantially similar design features in a mechanical joint are required or beneficial. The present invention joint has improved interior design, which uses a snap ring, a transfer gear with an enhanced thickness dimension, and a brake wheel comprising a central cutout area with a configuration complementary to that of the transfer gear's outer perimeter (and having each gear tooth clearly defined), wherein a portion of the transfer gear becomes press-fit into the central cutout area in the brake wheel during present invention joint use. The adjacent portion of the transfer gear not press-fit into the brake wheel is used to engage a gear configuration integral to the proximal end of the distal bar to produce a reducing gear ratio (preferably 2:1 in many orthotic applications) that allows a smaller stop increment than has been previously achieved in orthotic applications, as well as less travel of the distal bar between stops, less stress and wear on gear teeth, and enhanced joint strength. The integral gear configuration also simplifies construction and results in a more compact mechanical joint that provides cosmetic advantage in orthotic applications. In addition, less force is required to unlock it with a handle than is typically required for prior close contour joints. While prior and currently used orthotic devices typically have used a stop increment of approximately fifteen degrees, the internal design of the present invention has reduced its stop increment more than four-fold to approximately three degrees. In addition to having a distal bar configured for connection to orthotic hardware secured to the lower portion of a body limb (and movable between positions of complete flexion and full extension to provide the full 135 degree range of anatomical motion), the present invention joint also includes a T-bar configured for connection to orthotic hardware secured to the upper portion of a body limb and having a T-shaped proximal end secured within a T-shaped recess in the rear exterior surface of the joint's main body. The T-bar and T-shaped recess combination provide compact construction for an assembled joint to permit it to function less obtrusively. When the present invention joint is in its fully extended orientation, the T-bar extends from the joint in a direction substantially opposite to that of the distal bar. Furthermore, the distal bar and the T-shaped bar are pivotally connected to one another using a two axis (co-linear) construction (also a compactness-enhancing design improvement). In addition, the snap ring is opened by a user via a conveniently accessed handle that is connected to an unlocking pin with a non-symmetrical perimeter configuration providing multiple diameter dimensions that progressively move the snap ring open, and then smoothly allow it to close after further unlocking pin rotation occurs. The above-mentioned structure and other design features of the present invention make it compact, strong, efficient, visibly unobtrusive, and comfort-enhancing for its user. No other mechanical joint for orthotic use is known to have the same structure, function in the same manner, or provide all of the advantages of the present invention.

The description herein provides preferred embodiments of the present invention but should not be construed as limiting its scope. For example, variations in the diameter dimensions of the stop pin used, the number of gear teeth used in the transfer gear and the large gear configuration integral to the proximal end of the distal bar as long as a reducing ratio is achieved; the length, width, and thickness dimensions of the handle selected for use, the diameter dimensions of the pivot screws, and the dimensions and configuration of the T-shaped proximal end of the T-bar, other than those shown and described herein, may be incorporated into the present invention. Thus the scope of the present invention should be determined by the appended claims and their legal equivalents, rather than being limited to the examples given.

BRIEF DESCRIPTION OF THE SEVERAL VIEWS OF THE DRAWINGS

FIG. 8 is an enlarged view showing the relationship of interacting gears in the most preferred embodiment of the present invention that provide the advantageous reducing ratio (preferably 2:1 in many applications), with teeth on the larger gear configuration integral to the proximal end of the distal bar engaging a first portion of the transfer gear, further with the transfer gear having an enlarged thickness dimension that allows a second portion of it to be press-fit into a complementary cutout area centrally in the brake wheel, and also showing the snap ring with interior ratchet teeth in a position substantially around the exterior pawl surface of the brake wheel.

COMPONENT LIST IDENTIFYING REFERENCE NUMBERS USED IN THE DRAWINGS

Figure 1:
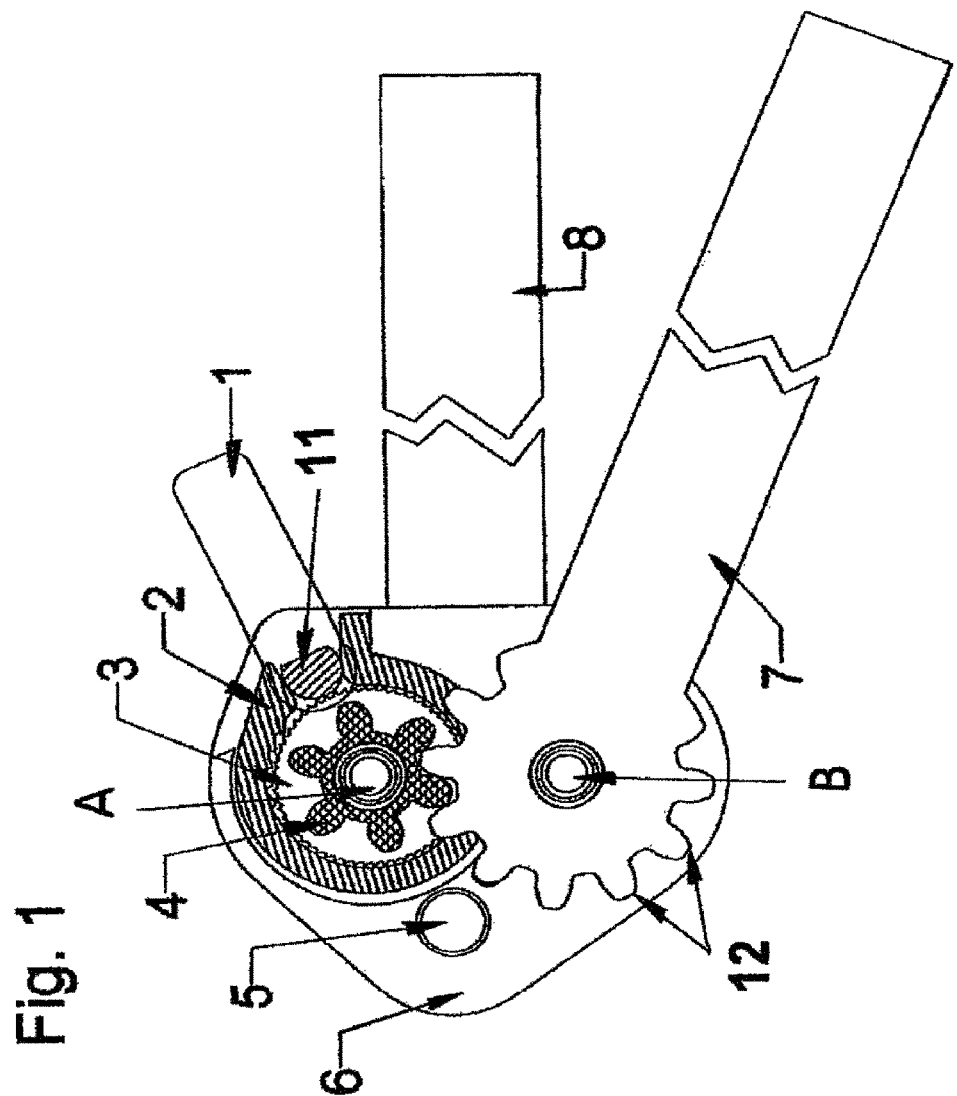
FIG. 1 is a front view of the most preferred embodiment of the present invention in a position allowing complete or near complete extremity flexion and showing its handle rotated into an unlocked position where the snap ring around the brake wheel is held open by the non-symmetrical perimeter configuration of an unlocking pin that in the unlocked position shown allows free rotation of the brake wheel, and corresponding free rotation of the distal bar relative to the T-bar from a position of full extension to a position of full flexion (the range of motion being approximately equal to the anatomical range of motion of 135 degrees), and since the present invention is in a position of maximum or near maximum extension, the stop pin shown is not in contact with any part of the distal bar.

1—handle (used to rotate the unlocking pin 11 that progressively forces snap ring 2 into its open position wherein the counterclockwise pointing ratchet teeth 16 of snap ring 2 are separated from the clockwise pointing teeth on the pawl surface 14 of brake wheel 3 to permit free rotational movement of brake wheel 3, with further rotation of unlocking pin 11 by handle 1 causing re-engagement of the ratchet teeth 16 of snap ring 2 with the pawl surface of brake wheel 3, wherein only stepped/ratcheted movement of brake wheel 3 can occur in the direction that causes distal bar extension)

2—snap ring (having counterclockwise pointing ratchet teeth 16 on its interior surface that are complementary in configuration to the clockwise pointing teeth on the pawl surface 14 exterior to brake wheel 3 for one-way movement of distal bar 7 toward maximum extension with small incremental stops, in many application reduced to approximately three degrees)

3—brake wheel (providing an exterior pawl surface 14 with teeth pointing in a clockwise direction that are adapted for engagement with the counterclockwise pointing ratchet teeth 16 of snap ring 2, and also providing a cutout interior surface 15 configuration that is complementary to the perimeter shape of transfer gear 4 so that when a portion of the transfer gear 4 is press-fit into the cutout interior surface 15, brake wheel 3 and transfer gear 4 rotate together, with a second portion of transfer gear 4 adjacent to that press-fit into brake wheel 3 being available for interaction with the larger gear configuration 12 integral to the proximal end of the distal bar 7 to produce a gear rotation reduction)

4—transfer gear (smaller of the two gears providing a reducing gear ratio in the present invention, preferably 2:1 in many contemplated applications, that provides the advantage of reducing the stop increment during extension movement of distal bar 7 for better simulation of natural body motion particularly for children and others with shorter legs, and also providing a more compact joint for less conspicuous presence and enhanced user comfort, reduced travel of distal bar 7 between stops that provides reduced stress on the ratchet teeth of snap ring 2, enhanced joint strength, and less user force required in employing handle 1 to unlock snap ring 2; with transfer gear 4 also having a thickened dimension, one portion of which is positioned to sequentially engage the teeth of the larger gear configuration 12 integral to the proximal end of distal bar 7 to provide a gear reduction ration, while a second adjacent portion of the thickened transfer gear 4 is press-fit into the cutout interior surface 15 of brake wheel 3 that is similar in configuration to the perimeter surface of transfer gear 4 and collectively includes the shape of all gear teeth present on transfer gear 4, with the press-fit connection allowing brake wheel 3 and transfer gear 4 to rotate together).

5—stop pin (is secured to main body 6 to limit rotation of distal bar 7 and block its movement beyond a position of maximum extension as distal bar 7 is moved away from T-bar 8 and toward its position of full extension)

6—main body (has a T-shaped recess 17 in its exterior surface that is complementary in configuration to the T-shaped proximal end 13 of T-bar 8 for compactly securing T-bar 8 against main body 6 with the T-shaped proximal end 13 secured to both of the co-linear axes of rotation marked as "A" and "B" that enhance joint strength, with the main body 6 also configured so that the T-shaped proximal end 13 can be fastened to it with two pivot screws 10)

7—distal bar (its proximal end is configured with a larger gear configuration 12 that engages smaller transfer gear 4 to provide an advantageous a reducing gear ratio, preferably 2:1 in many orthotic applications, that can reduce the approximate six degrees of rotation for each ratcheted step of brake wheel 3 movement to very small distal bar 7 incremental stops of only three degrees)

8—"T" bar (it has a T-shaped proximal end 13 adapted for strong and space-saving connection to a T-shaped recess 17 in the external surface of main body 6 in part by facilitating a co-linear axis configuration)

9—main cover (it is secured against main body 6 by pivot screws 10 and provides protection for all moving internal parts in the present invention close contour mechanical joint from damaging contact, as well as malfunction resulting from the presence of dirt and debris)

10—pivot screws (secure main cover 9 and the T-shaped proximal end 13 of T-bar 8 to main body 6)

11—unlocking pin (it is rotated by user movement of handle 1 to unlock snap ring 3 from its close positioning around the exterior pawl surface of brake wheel 3 and has a non-symmetrical perimeter configuration 18 with multiple diameter dimensions that are used to progressively force snap ring 3 open and thereafter allow it to smoothly close as unlocking pin 11 is further rotated)

12—the larger gear configuration integral to the proximal end of distal bar 7 (together with transfer gear 4 it provides the preferred advantageous gear ratio reduction of approximately 2:1 for improved joint strength and less stress/wear for components)

13—T-shaped proximal end of T-bar 8 (it is complementary in configuration to the T-shaped recess 17 formed into the exterior surface of main body 6 and it is secured within the T-shaped recess 17 via use of two pivot screws 10 each positioned at one of the co-linear axes of rotation for distal bar 7 relative to T-bar 8, marked by the designations of "A" and "B" in the accompanying illustrations)

14—exterior pawl surface of brake wheel 3 (has teeth pointing in a clockwise direction for engagement with the counterclockwise pointing ratchet teeth 16 of snap ring 2 to prevent movement of brake wheel 3 and thereby prevent flexion movement of distal bar 7 in a direction toward T-bar, instead only allowing movement of distal bar 7 with small incremental stops in a direction away from T-bar 8 and toward the pre-determined position of maximum extension, typically representative of the full 135-degree range of anatomical motion)

15—interior surface of brake wheel 3 (has a cutout configuration complementary to the perimeter shape of transfer gear 4 that allows brake wheel 3 and transfer gear 4 to rotate together when a portion of the thickened transfer gear 4 is press-fit into the cutout area) 16—ratchet teeth on the interior surface of snap ring 2 (that are counterclockwise pointing and complementary in configuration to the clockwise pointing teeth on the exterior pawl surface 14 of brake wheel 3 for engagement therewith when handle 1 is positioned to lock snap ring 2 and brake wheel 3 together to prevent free movement of brake wheel 3)

17—T-shaped recess in main body 6 (it receives the T-shaped proximal end 13 of T-bar 8 with secure fastening therebetween achieved via two pivot screws 10)

18—non-symmetrical perimeter configuration of unlocking pin 11 (has multiple diameter dimensions that progressively force snap ring 2 open as handle 1 rotates it, and thereafter allows snap ring 2 to smoothly close around brake wheel 3 as unlocking pin 11 is further rotated by handle 1)

A—axis of rotation for the transfer gear 4 and also an anchoring point for the T-shaped proximal end 13 of T-bar 8 (it is co-linear to the axis of rotation B for distal bar 7)

B—axis of rotation for the distal bar 7 and also an anchoring point for the T-shaped proximal end 13 of T-bar 8 (it is co-linear with the axis of rotation A for the T-shaped proximal end 13 of T-bar 8)

DETAILED DESCRIPTION OF THE INVENTION

The present invention provides a close contour mechanical joint that better simulates natural body motion through use of a smaller stop increment for its distal bar 7 movement, making it particularly effective in pediatric applications to assist an inadequately functioning body limb. However, the present invention is also effective for other orthotic applications, as well as use in any device needing a mechanical joint for which the compact configuration and/or strength of the present invention would provide some assistance or technical advantage. The present invention joint has improved interior design, which uses a snap ring 2, a brake wheel 3, and a transfer gear 4 that is partially press-fit into a central cutout area (having interior surface 15) within brake wheel 3, and which comprises shape complementary to the portion of the transfer gear 4 perimeter collectively defined by its teeth. Transfer gear 4 is used in combination with a larger gear configuration 12 integral to the proximal end of the movable distal bar 7 to produce a reducing gear ratio (preferably 2:1 in many orthotic applications) that allows a smaller stop increment than has been previously achieved in orthotic applications, as well as less travel of the distal bar 7 between stops, less stress on gear teeth (such as 14, and 16), and enhanced joint strength. In addition, less force is required to unlock the present invention close contour mechanical joint with a handle 1 than is typically required for previously constructed close contour joints. While prior art devices typically have used a stop increment of approximately fifteen degrees, the internal design of the present invention has reduced its stop increment more than four-fold to approximately three degrees, which is accomplished by its advantageous gear ratio reduction and is a very significant improvement. Initially, each ratcheted step between teeth on snap ring 2 and the exterior pawl surface of brake wheel 3 provide approximately six degrees of rotation. However, the gear ration reduction of approximately 2:1 provided by transfer gear 4 and the larger gear configuration 12 integral to the proximal end of the movable distal bar 7 allows a smaller stop increment for distal bar 7 movement of approximately three degrees. Simply making the teeth on brake wheel 3 and snap ring 2 smaller to provide ratcheted steps of three degrees is not a viable alternative for orthotic use, as problems with joint strength and excessive gear teeth wear are encountered. In addition to having a distal bar 7 configured for connection to orthotic hardware attached to the lower portion of a body limb and moving between positions of complete flexion and full extension (approximately the full 135 degree range of anatomical motion), the present invention joint also includes a T-bar 8 configured for connection to orthotic hardware attached to the upper portion of a body limb and having a T-shaped proximal end 13 that is secured within a T-shaped recess 17 in the exterior surface of the joint's main body 6. One of two pivot screws 10 used to attach the T-shaped proximal end 13 of T-bar 8 to main body 6, as well as the main cover 9 to main body 6, and which also provides the axis of rotation marked as "B", is further used to secure the distal bar 7 in working relation within main body 6. When the present invention close contour mechanical joint is in its fully extended orientation, the T-bar 8 extends from main body 6 in a direction opposite to that of the distal bar 7. Furthermore, the distal bar 7 and the T-shaped bar 8 are pivotally connected to one another using the space-saving two axis (co-linear) construction (A, B), and the snap ring 2 is opened by a user via a handle 1 that is connected to an unlocking pin 11 having a non-symmetrical perimeter configuration 18 that provides multiple diameter dimensions configured for progressively moving snap ring 2 into an open configuration where its ratchet teeth 16 become separated sufficiently from the pawl surface 14 of brake wheel 3 to allow free movement of brake wheel 3, as well as corresponding free movement of distal bar 7 relative to T-bar 8. Further rotation of unlocking pin 11 via handle 1 allows snap ring 2 to smoothly close again around the exterior pawl surface 14 of brake wheel 3 and for the clockwise pointing teeth on the pawl surface 14 of the exterior surface of the brake wheel 3 to firmly engage the counterclockwise pointing ratchet teeth 16 on the interior surface of snap ring 2. The multiple design features of the present invention in combination make it compact, strong, efficient, visibly unobtrusive, and comfort-enhancing for its user.

Figure 4:
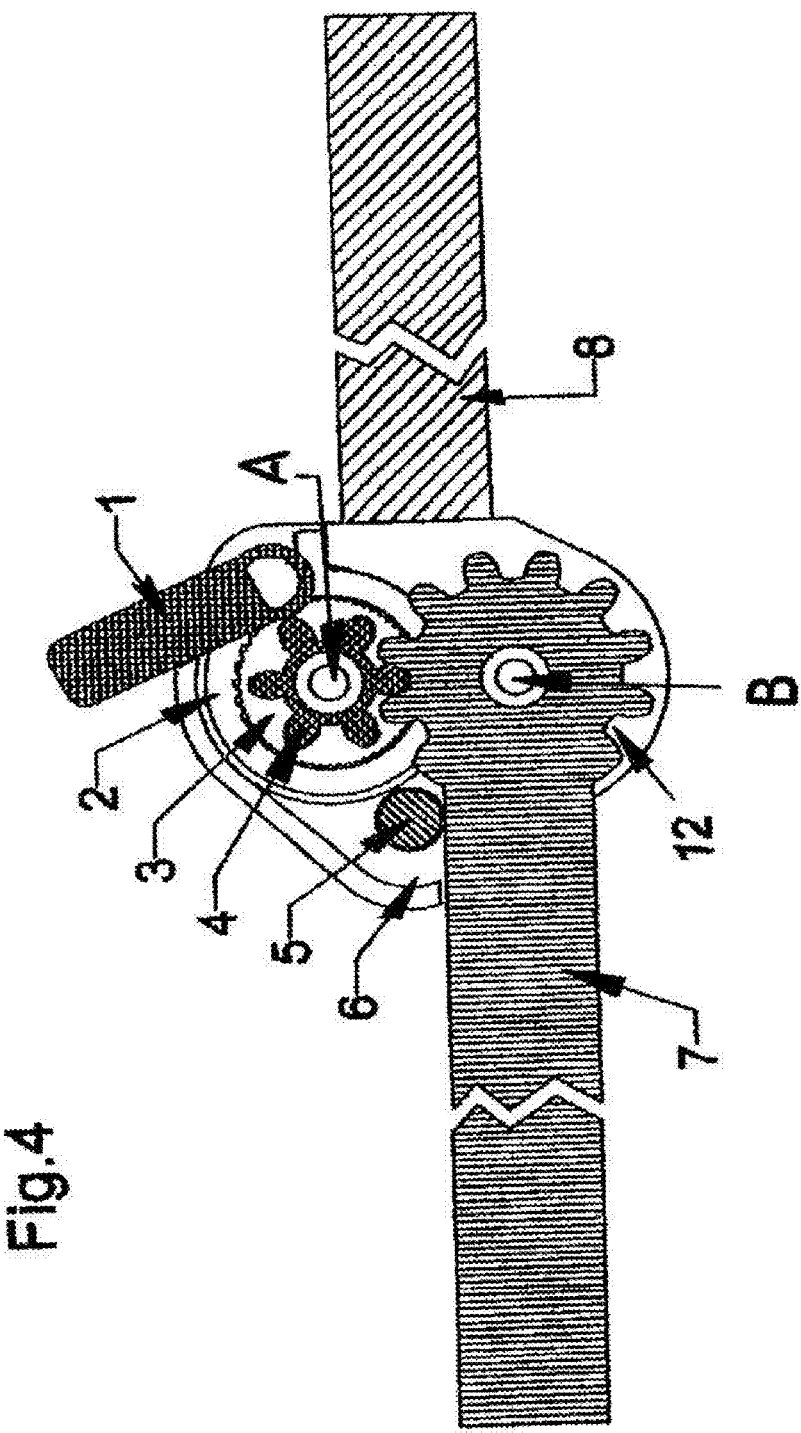
FIG. 4 is a sectional view of the most preferred embodiment of the present invention in a position of maximum or near maximum extension and showing teeth on the smaller transfer gear engaging teeth on the larger gear configuration integral to the proximal end of the distal bar to provide a reducing gear ratio of approximately 2:1, which creates a strong resistance to flexion and is able to downwardly adjust the distal bar stop increment to approximately three degrees from the original six degrees of rotation provided by each ratcheting movement of the brake wheel, with rotation of the distal bar continuing in increments of approximately three degrees until maximum extension is reached wherein the distal bar and the T-bar extend in opposing directions from the main body and the stop pin blocks further travel of the distal bar away from the T-bar.
Figure 5:
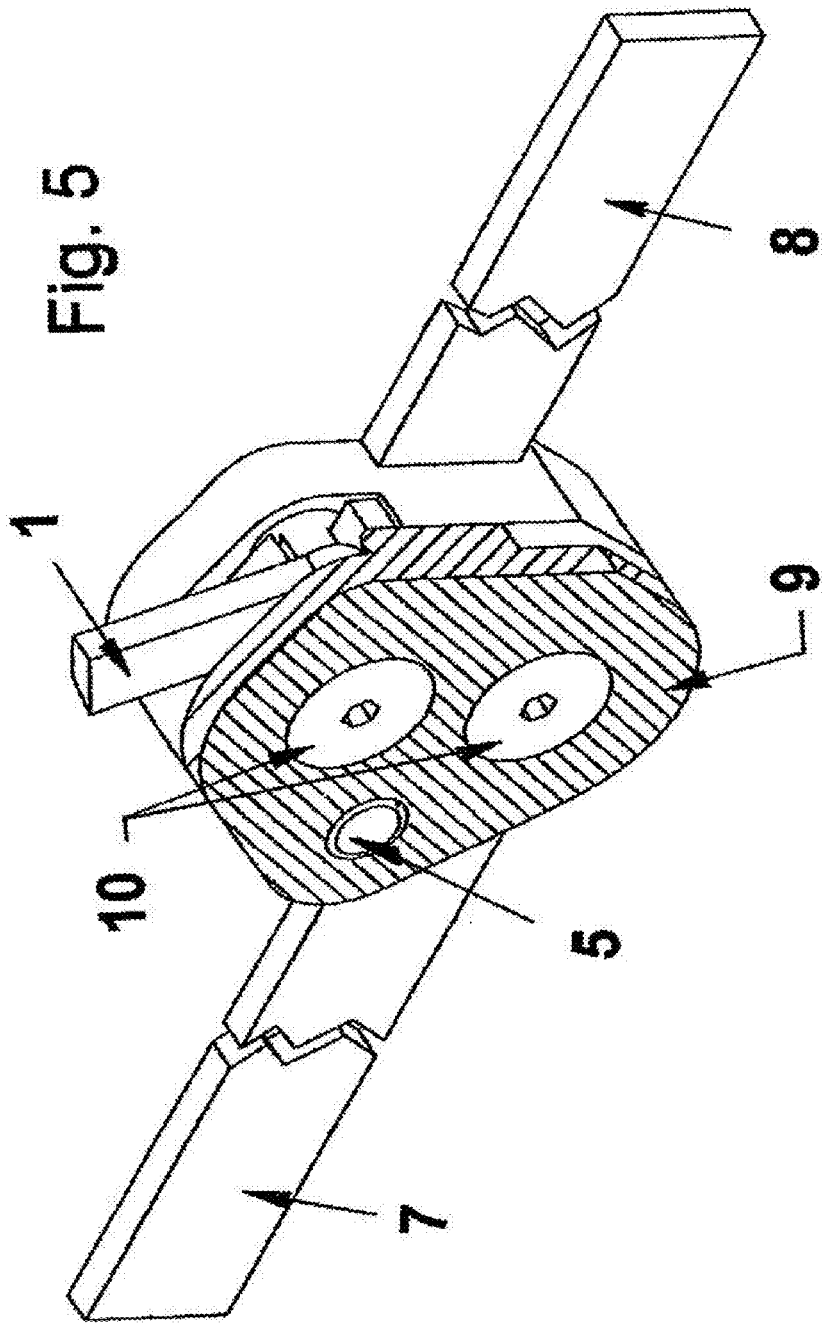
FIG. 5 is an isometric view of the most preferred embodiment of the present invention mechanical joint in FIG. 4 with FIG. 5 also showing an outer cover (hereinafter also referred to as main cover) held securely in place to the joint's main body with pivot screws, wherein the main body in the preferred position of use shown provides joint stability and also protects the transfer gear, the large gear configuration integral to the proximal end of the distal bar, the brake wheel, and the snap ring from damaging contact, as well as interference from dirt and debris.
Figure 6:
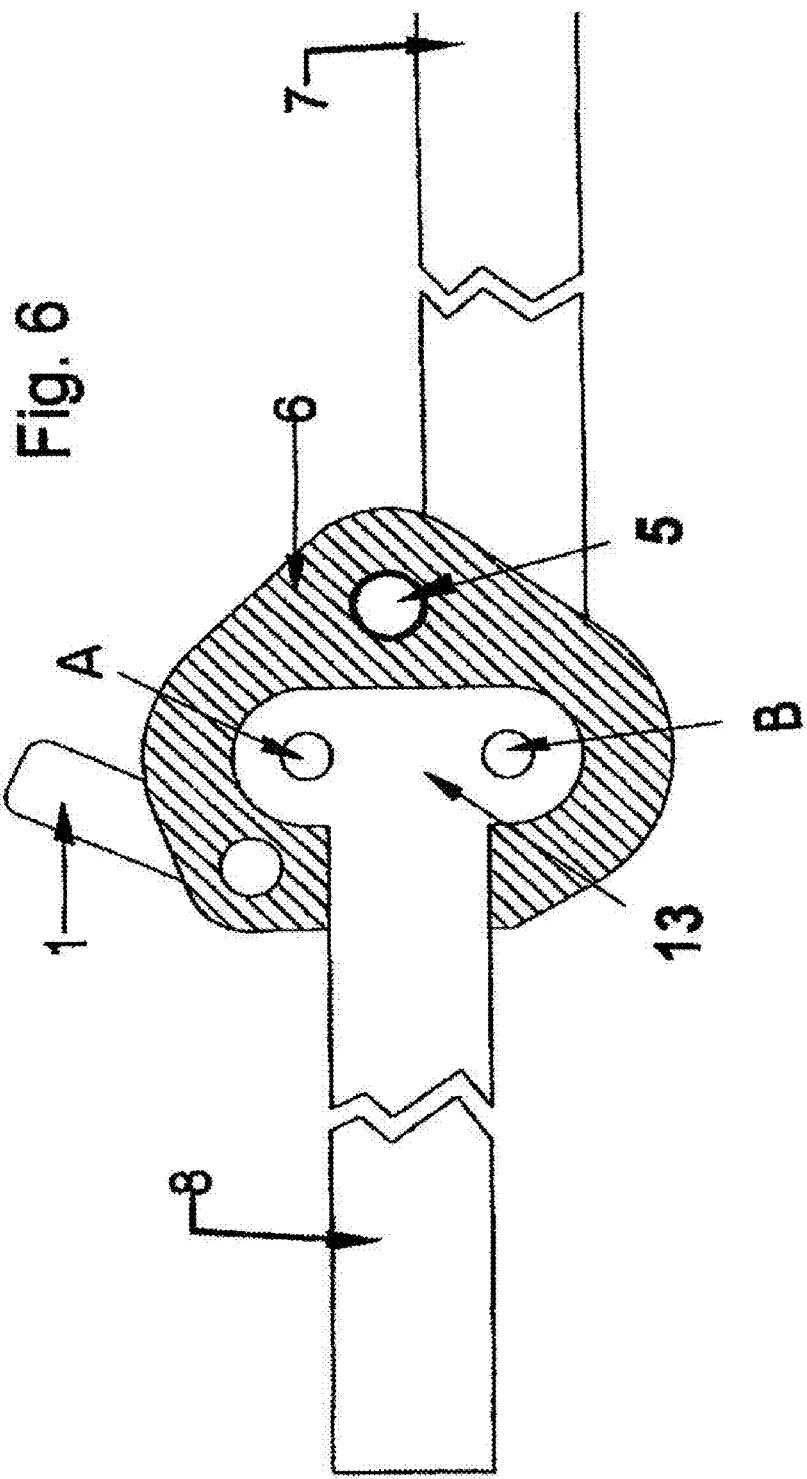
FIG. 6 is a rear view of the main body of the most preferred embodiment of the present invention shown in FIG. 5, with FIG. 6 showing secure attachment of the T-shaped configuration of the T-bar's proximal end into a T-shaped recess in the main body of the present invention close contour mechanical joint.
Figure 7:
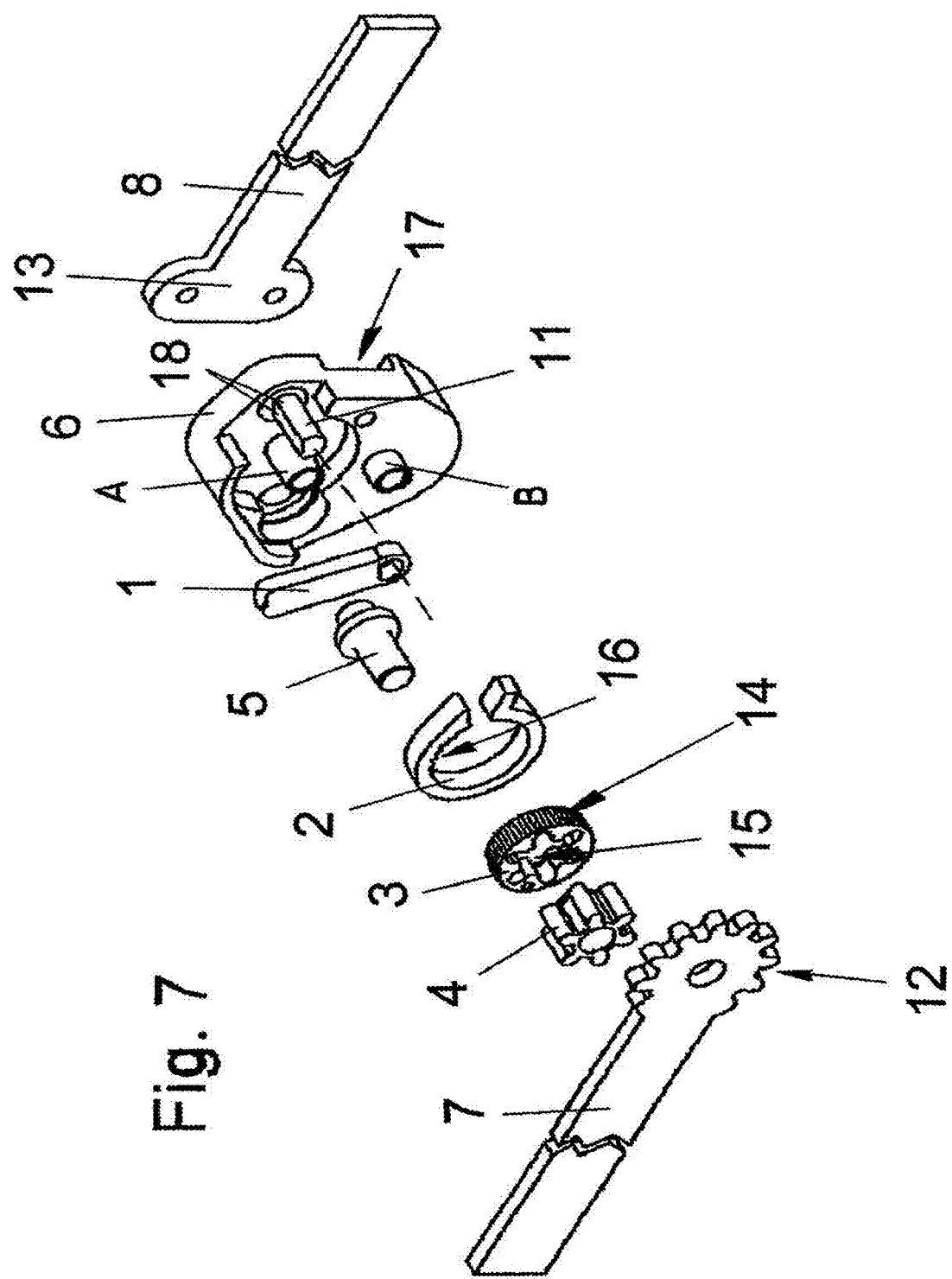
FIG. 7 is an exploded view of the most preferred embodiment of the present invention shown in FIG. 4, with FIG. 7 showing the sculptured interior side of the main body, as well as the enlarged thickness of the transfer gear that allows it to be partially press-fit into the central cutout area in the brake wheel, with the other portion of the transfer gear configured to engage teeth on the larger gear configuration integral to the proximal end of the distal bar, and further with a broken line showing the intended connection between a user-operated handle and the unlocking pin that when rotated releases the snap ring from its otherwise tight engagement around the brake wheel, and also with the letters "A" and "B" designating the co-liner axis construction of the present invention close contour mechanical joint.

FIG. 1 is a front view of the most preferred embodiment of the present invention in a position allowing complete extremity flexion that is approximately equivalent to the 135 degrees of anatomical motion of the lower leg. Thus, when the present invention close contour mechanical joint is fully flexed, the resulting angle between distal bar 7 and T-bar 8 is approximately forty-five degrees. FIG. 1 also shows handle 1 rotated into an unlocked position where the snap ring 2 around the brake wheel 3 is held open by a larger diameter portion of the non-symmetrical perimeter configuration 18 (see numbered component in FIG. 7) of a unlocking pin 11, so that free rotation of brake wheel 3 is allowed without engagement of the ratchet teeth 16 on the interior surface of snap ring 2 against the exterior pawl surface 14 of brake wheel 3. Handle 1 can then be used to lock in any needed angle between distal bar 7 and T-bar 8, including full flexion. Since the teeth on the pawl 14 of the brake wheel 3 are clockwise pointing and the ratchet teeth 16 of snap ring 2 are counterclockwise pointing, movement of distal bar 7 relative to T-bar 8 with incremental stops is exhibited only in one direction (during extension when distal bar 7 moves father away from T-bar 8, such as when a person uses the present invention close contour mechanical joint with a knee and rises from a seated to a standing position). The stop pin 5, in combination with engagement of the gear teeth of transfer gear 4 with those of the larger gear configuration integral to the proximal end of distal bar 7, provide substantial support of a user when the present invention joint nears maximum extension. Furthermore, the substantial support of a user at or near a position of full extension continues until the user employs handle 1 to rotate unlocking pin 11 and move snap ring 2 into its open position where brake wheel 3 moves freely, and allows corresponding free movement of distal bar 7 relative to T-bar 8 from positions of full extension to full flexion, and vice versa (in a range of motion equal to the anatomical range of motion, approximately 135 degrees). The main cover 9 (shown in FIG. 5) is removed in FIG. 1 so that snap ring 2, brake wheel 3, transfer gear 4, the connection of unlocking pin 11 to the proximal end of handle 1, stop pin 5, and the larger gear configuration 12 integral to the proximal end of distal bar 7, are all visible. Main cover 9 protects internal components of the present invention from damaging contact, as well as any moving component malfunction resulting from dirt and debris in main body 6 that might otherwise accumulate unless main cover 9 is properly affixed into its preferred position of use. It is the engagement of the teeth of transfer gear 4 with those of the larger gear configuration 12 integral to the proximal end of distal bar 7 that provides the advantageous gear reduction ratio (preferably 2:1 in many orthotic applications) that allows the stop increment of the present invention close contour mechanical joint to be reduced to approximately three degrees. FIG. 1 also shows the axis of rotation A provided by main body 6 for T-bar 8, which is co-linear to the axis of rotation B provided for distal bar 7. As shown in FIGS. 5 and 6, the same two pivot pins 10 that secure main cover 9 to main body 6 are both used to secure the T-shaped configuration on the proximal end of T-bar 8 to main body 6. In contrast, only one of the pivot pins 10 (that associated with axis of rotation B) engages distal bar 7. As distal bar 7 moves out of the position of full flexion shown in FIG. 1 and away from T-bar 8, a position of full extension will be defined by stop pin 5 which is located on main body 6 to contact distal bar 7 and block further movement away from T-bar 8 beyond a pre-selected position of maximum extension (typically equal to the full 135-degree range of anatomical motion for orthotic applications). However, although the preferred interior placement of stop pin 5 within main body 6 is shown in FIG. 1, it is not contemplated for the size and placement of stop 5 shown in FIG. 1 to be critical. More detail about the relationship of the stop pin 5 and the main body 6 used in the most preferred embodiment of the present invention is shown in FIG. 7. As shown in FIG. 4, it is the engagement of stop pin 5 with a portion of the proximal end of distal bar 7 adjacent to its gear teeth that defines the limit of extension movement for distal bar 7. Materials for all components shown in FIG. 1 should have enhanced strength, enhanced resistance to wear, efficient operation is a wide range of ambient temperatures, and the capability of withstanding repeated exposure to humid environments without premature deterioration.

Figure 2:
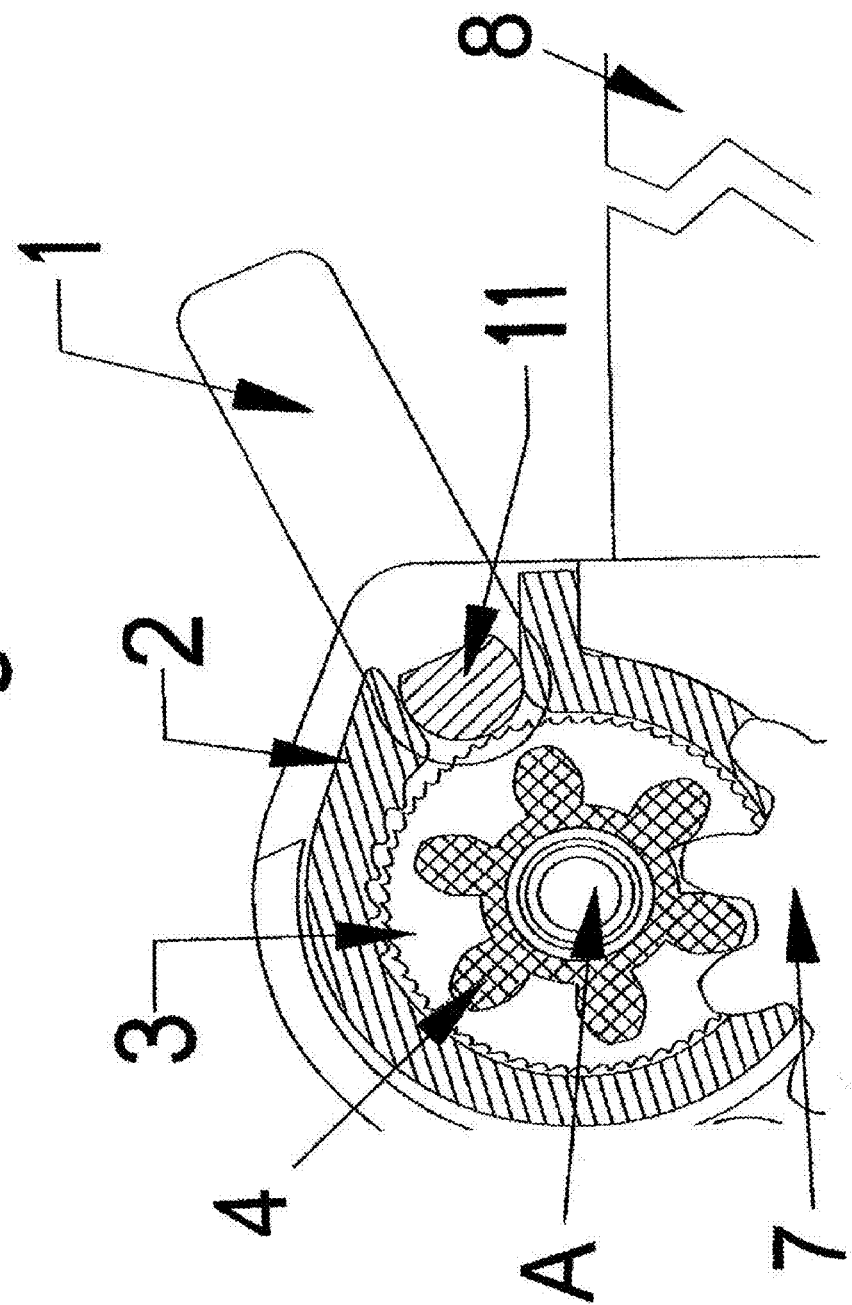
FIG. 2 is an enlarged view of the most preferred embodiment of the present invention in FIG. 1 and showing the present invention unlocking pin associated with a handle in substantially the same rotated position shown in FIG. 1 that causes the snap ring to be held open, thereby permitting disengagement of the counterclockwise pointing ratchet teeth on the interior surface of the snap ring from the complementary pawl surface on the exterior surface of the brake wheel (that has teeth pointing in a clockwise direction).
Figure 3:
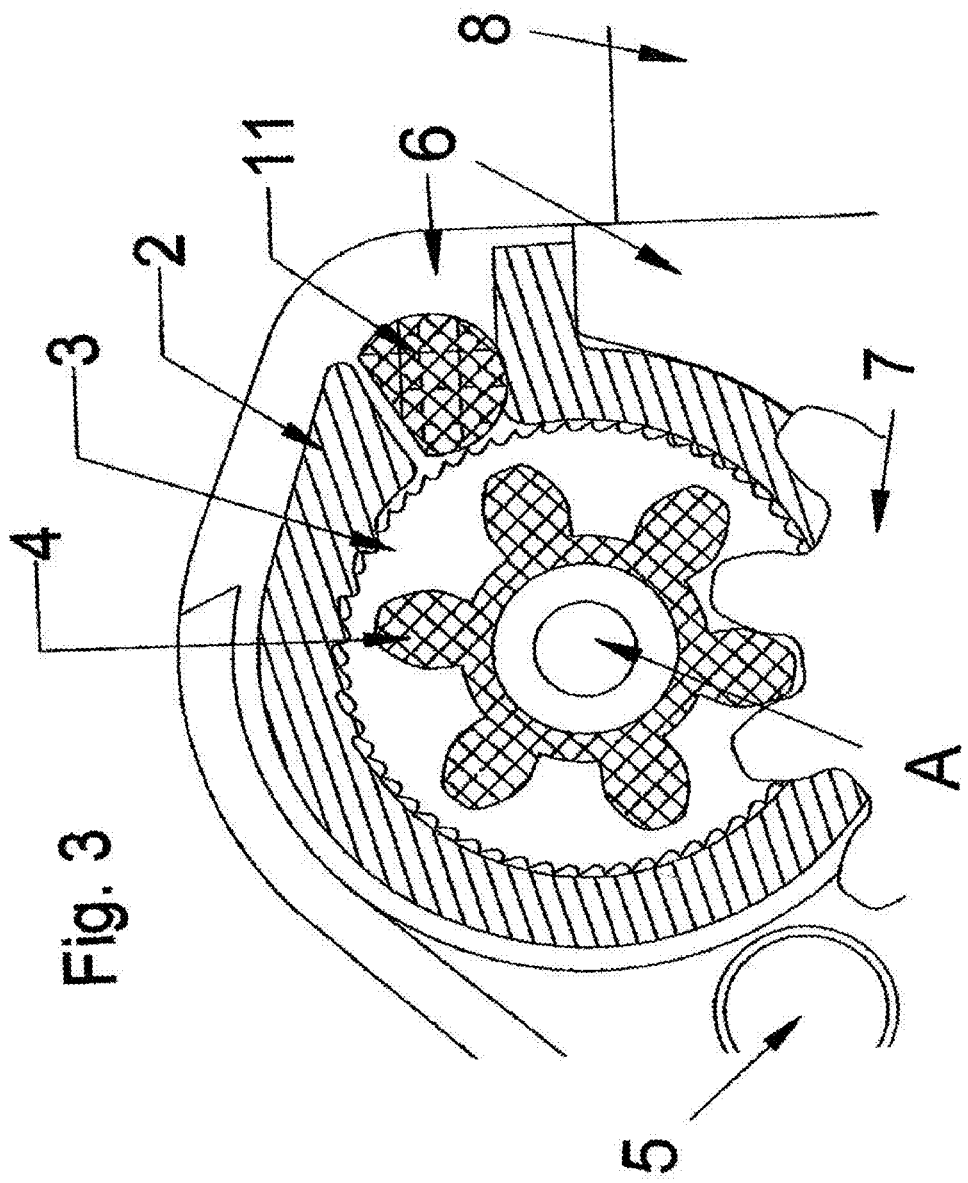
FIG. 3 is an enlarged view of the most preferred embodiment of the present invention showing a changed orientation for the unlocking pin from that shown in FIGS. 1 and 2, with the new locking position allowing the ratchet teeth on the interior surface of the snap ring to engage the exterior pawl surface on the brake wheel and provide a close fit of the snap ring around the exterior surface of the brake wheel, with FIG. 3 also showing the angle of the teeth on snap ring and brake wheel allowing a ratcheting motion in one direction only (towards maximum extension of the associated distal bar), with each ratcheting step moving the brake wheel through approximately six degrees of rotation and the resulting motion of the brake wheel causing the transfer gear press-fit centrally into the brake wheel to rotate, which in combination with the larger gear configuration integral to the proximal end of the distal bar will preferably cause a gear ration reduction of the approximately six degrees ratcheting step to a stop increment for the distal bar of approximately three degrees.

FIGS. 2 and 3 are enlarged views of the most preferred embodiment of the present invention in FIG. 1 and show the unlocking pin 11 associated with proximal end of handle 1 in differing positions. In FIG. 2, unlocking pin 11 is in a rotated position (similar to that shown in FIG. 1) that causes the snap ring 2 to be held open so that the ratchet teeth 16 on the interior surface of snap ring 2 become sufficiently disengaged from the complementary pawl surface 14 on the exterior of brake wheel 3, and thereby allow free motion of brake wheel 3 (and corresponding free movement of distal bar 7 relative to T-bar 8). As can be clearly seen in FIGS. 2 and 3, it is preferred for the teeth on pawl surface 14 to point in a clockwise direction and only allow the small incremental stops for distal bar 7 during its movement toward a position of maximum extension, and away from T-bar 8. In contrast, FIG. 3 is an enlarged view of the most preferred embodiment of the present invention showing the unlocking pin 11 rotated into a position that allows the ratchet teeth 16 on the interior surface of snap ring 2 to more closely engage the exterior pawl surface 14 on brake wheel 3, so that free movement of brake wheel 3 is prevented (and free movement of distal bar 7 relative to T-bar 8 is also prevented), and instead only distal bar 7 movement with small incremental stops is allowed to occur until the operator intervenes by adjusting handle 1 or the position of full extension is reached. FIG. 3 also best shows the angle of the ratchet teeth 16 (identified by number in FIG. 7) on snap ring 2 in a clockwise direction (better than any of the other accompanying illustrations), in addition to providing the most detailed views of the exterior pawl surface 14 on brake wheel 3 that has a complementary configuration to ratchet teeth 16 and allows a ratcheting motion in only one direction (that allowing distal bar 7 to move toward its position of maximum extension), with each ratcheting step preferably providing approximately six degrees of rotation for orthotic use. It is the gear ratio reduction provided in part by transfer gear 4 that creates the smaller incremental stops for distal bar 7 movement of approximately three degrees. FIGS. 2 and 3 also show transfer gear 4 centrally press-fit into central portion of brake wheel 3, so that transfer gear 4 moves in concert with brake wheel 3. Thus, the motion of brake wheel 3 relative to snap ring 2 that is allowed when unlocking pin 11 releases the firm grip of snap ring 2 around brake wheel 3 forces the transfer gear 4 to also move with brake wheel 3. Since transfer gear 4 has a thickened configuration and only a portion of it press-fit into brake wheel 3, the teeth on the portion of transfer gear 4 not press-fit into brake wheel 3 are available for sequentially engaging teeth on the larger gear configuration 12 integral to the proximal end of distal bar 7 as distal bar moves in either direction, in a direction of increased flexion toward T-bar 8 or in a direction of increased extension away from T-bar 8. Thus, when unlocking pin 11 is in the position shown in FIG. 2, free movement of distal bar 7 is possible between positions of full flexion and full extension relative to T-bar 8. However, in contrast, when unlocking pin 11 is in the position shown in FIG. 3, movement of distal bar 7 is only permitted in the direction of full extension with small incremental stops (typically three degrees in many orthotic applications). FIGS. 2 and 3 each show very little of T-bar 8 or distal bar 7, however the axis of rotation A for T-bar 8 is clearly shown in both illustrations (which is co-linear to the axis of rotation B of the distal bar 7 shown in other illustrations). FIGS. 2 and 3 also clearly show the close press-fit arrangement of transfer gear 4 centrally within brake wheel 3, as well as the engagement its teeth to those of the larger gear configuration 12 integral to the proximal end of distal bar 7, which together provide a gear ratio reduction (2:1 or other). Additionally, FIG. 3 shows a preferred location of pin stop 5 and a numeral 6 that is used to identify various portions of main body 6. To enhance the clarity of the alternative positioning for unlocking pin 11 shown in FIG. 3, handle 1 was purposefully omitted.

FIG. 4 is a sectional view of the most preferred embodiment of the present invention showing distal bar 7 in a position of full extension from T-bar 8. FIG. 4 also shows the teeth on the smaller transfer gear 4 engaging teeth on the larger gear configuration 12 integral to the proximal end of the distal bar 7 to provide preferred gear ratio reduction of approximately 2:1, which creates a strong resistance to flexion and adjusts each rotational stop for distal bar 7 as it moves away from T-bar 8 toward a position of maximum extension to approximately three degrees of rotation, with rotation continuing in increments of approximately three degrees until the stop pin 5 blocks further travel of distal bar 7 when it reaches the position of full extension (equivalent to the approximate 135 degrees of anatomical rotation). FIG. 4 also shows handle 1 in a position allowing closure of snap ring 2 around brake wheel 3, with a firm connection established between the ratchet teeth 16 (identified by number in FIG. 7) on snap ring 2 engages the exterior pawl surface 14 on brake wheel 3. Distal bar 7 cannot be moved out of the position of full extension, until handle 1 is used to rotate locking pin 11 a sufficient amount to separate ratchet teeth 16 on snap ring 2 from the exterior pawl surface 14 on brake wheel 3 and thereby provide free movement of brake wheel 3 (and free movement of distal bar 7 relative to T-bar 8). In addition, FIG. 4 shows a numeral 6 pointing to one portion of main body 6 to generally identify it. Also in FIG. 4, the axis of rotation associated with T-bar 8 is identified by the letter "A", and it is shown in a co-linear arrangement with the axis of rotation B for the distal bar 7 that is identified by the letter "B".

FIG. 5 is a front view, in isometric orientation, of the most preferred embodiment of the present invention in FIG. 4, with distal bar 7 shown in a position of full or near full extension from T-bar 8. FIG. 5 also shows the present invention having an outer cover (also referred to as main cover 9) that is held securely in place with two pivot screws 10 to provide stability and protection for moving parts positioned for use between main cover 9 and main body 6. FIG. 5 shows the preferred location of pin stop 5 in the present invention close contour mechanical joint, and handle 1 in a position that allows a close fit of the ratchet teeth 16 (identified by number in FIG. 7) on snap ring 2 around the exterior pawl surface 14 on brake wheel 3, and only movement with incremental stops in the direction of extension can occur for distal bar 7 unless handle 1 is manipulated to change the positioning of unlocking pin 11. However, since FIG. 5 shows T-bar 8 and distal bar 7 in substantially opposing positions at or very close to a position of maximum extension, little or no additional movement of distal bar 7 relative to T-bar 8 will take place in the direction of complete flexion until handle 1 is used to permit free movement of brake wheel 3. FIG. 5 also shows the pivot screw 10 located closest to handle 1 at the axis of rotation associated with T-bar 8 (marked by the designation of "A" in FIGS. 4 and 6), and the other pivot screw 10 located at the axis of rotation for distal bar 7 (marked by the designation of "B" in FIGS. 4 and 6). Although not marked with a numerical designation, FIG. 5 further shows each pivot screw 10 having a central hex indentation that facilitates prompt and secure tightening of pivot screw 10, as well as its prompt removal when needed. The use of a hex indentation on pivot screws 10 is merely provided as an example, and any geometric or other non-slip configuration can also be alternatively employed.

FIG. 6 is a rear view of the main body 6 of the most preferred embodiment of the present invention shown in FIG. 5 with distal bar 7 shown in a position of full or near full extension from T-bar 8. FIG. 6 also shows receipt of the T-shaped configuration 13 of the T-bar 8 within a T-shaped recess in main body 6 (identified and marked by the numerical designation of "17" in FIG. 7). FIG. 6 further shows the axis of rotation "A" associated with T-bar 8 in a co-linear arrangement with the axis of rotation "B" for the distal bar 7. It is contemplated for the pivot screws 10 (shown in FIG. 5) extending through the axes of rotation "A" and "B" to be used to securely fix the T-shaped configuration 13 of T-bar 8 against main body 6, as well as main cover 9 against main body 6. The preferred location of pin stop 5 for blocking further extension of distal bar 7 at a designated position of full extension (typically the full 135-degrees of anatomical motion) from T-bar 8 is also shown in FIG. 6, and a numeral 1 being used for identifying handle 1 that is in an orientation indicating closure of snap ring 2 around brake wheel 3, so that the ratchet teeth 16 (identified by number in FIG. 7) on snap ring 2 firmly engage the exterior pawl surface 14 on brake wheel 3.

FIG. 7 is an exploded view of the most preferred embodiment of the present invention shown in FIG. 4, and showing the preferred sculptured internal configuration of main body 6, as well as the enlarged thickness of transfer gear 4 relative to brake wheel 4 (so that only a portion of transfer gear 4 is press-fit centrally into brake wheel 3 and the adjacent portion remains available to engage the larger gear configuration 12 on the proximal end of distal bar 7. Thus, when handle 1 is moved to rotate unlocking pin 11, so that its non-symmetrical perimeter configuration opens snap ring 2 a sufficient amount to separate the ratchet teeth 16 on snap ring 2 from the exterior pawl surface 14 on brake wheel 3, brake wheel 3 is able to freely move (thus allowing corresponding free movement of distal bar 7 between positions of full flexion and maximum extension. In contrast, when the present invention mechanical joint is locked, brake wheel 3 only advances one ratcheted step (an incremental amount defined by the size and configuration of the clockwise teeth 16 on the pawl surface 14 of brake wheel 3 in combination with the complementary ratchet teeth 14 on the interior surface of snap ring 2 and preferably equivalent to approximately six degrees of rotation), which advances the transfer gear 4 in fixed press-fit relation to brake wheel 3 by the same incremental amount. As the teeth on transfer gear 4 engage the teeth on the larger gear configuration 12 integral to the proximal end of distal bar 7 that together provide a gear ratio reduction (preferably 2:1 for many orthotic applications), the incremental amount of rotation transferred to distal bar 7 is reduced to approximately three degrees, and provides a smooth extension of distal bar 7 away from T-bar 8. FIG. 7 generally shows the order of assembly for the components of the present invention close contour mechanical joint, with the exception of main cover 9 and pivot screws 10, which if shown would be positioned to the left of distal bar 7. FIG. 7 shows distal bar 7 in the leftmost position with the central opening (un-numbered) in its larger gear configuration 12, which would become associated with rotation axis "B", is purposefully shown in a lowered position that is not in alignment with the longitudinal axis of transfer gear 4 (nor that of brake wheel 3 or that of snap ring 2), since it is contemplated that all three would be associated with axis of rotation marked by the designation of "A". FIG. 7 further shows pin stop 5 and handle 1 not in alignment with either axis of rotation "A" or axis of rotation "B", with pin stop 5 being off-set so that it can be placed adjacent to the gear teeth on distal bar 7 at a position of maximum extension to block further movement of distal bar 7 away from T-bar 8. Although the portion of main body 6 where it is preferred for pin stop 5 to be secured is not marked with a number, in FIG. 7 it is located immediately to the left of axis of rotation "A". A broken line in FIG. 7 shows the intended connection between a user-operated handle 1 and the unlocking pin 11 with a non-symmetrical perimeter configuration with multiple diameter dimensions that when rotated progressively releases the snap ring 2 from its otherwise tight engagement around brake wheel 3. Although the non-symmetrical perimeter configuration shown for unlocking pin 11 is preferred, it is not critical and other non-symmetrical perimeter configurations can also be used. FIG. 7 also shows a recess 17 in the rearward-extending surface of main body 6 that is similar in size and configuration to the T-shaped proximal end 13 of T-bar 8, so that a secure press-fit connection can be made between recess 17 and T-bar 8, including its T-shaped proximal end 13. The pivot screws 10 used to secure main cover 9 to main body 6 would also help to maintain T-shaped proximal end 13 in a secure fixed position within T-shaped recess 17.

FIG. 8 is an enlarged view showing the relationship of interacting gears in the most preferred embodiment of the present invention that provide the advantageous gear ratio reduction (preferably 2:1 in many orthotic applications). Main cover 9, main body 6, and handle 1 are not illustrated in FIG. 8. However, FIG. 8 does show the teeth on the larger gear configuration 12 integral to the proximal end of the distal bar 7 engaging teeth on the portion of transfer gear 4 situated adjacent to brake wheel 3, but not press-fit into it. Since the width dimension of the portion of transfer gear 4 visible in FIG. 8 is nearly identical to that shown for brake wheel 3, but when viewed in FIG. 7 the transfer gear 4 is shown to have a much thicker dimension than brake wheel 3, one can easily conclude that the rear half of transfer gear 4 is press-fit centrally into brake wheel 3 in FIG. 8. FIG. 8 further shows snap ring 2 positioned substantially around the exterior pawl surface (marked by the number 14 in FIG. 7) of brake wheel 3, with the ratchet teeth (marked by number 16 in FIG. 7) on snap ring 2 engaging the exterior pawl surface 14 on brake wheel 3. The un-numbered void area between the ends of snap ring 2 that reveals a portion of the exterior pawl surface 14 of brake wheel 3, is the preferred position of use for unlocking pin 11.

We claim:

1. A strong mechanical joint for use with orthotic hardware, said mechanical joint comprising:
   a housing with interior space;
   a distal bar associated with said housing so as to create a first axis of rotation, said distal bar having a proximal end and an opposed end, said distal bar also having a large gear configuration integral to said proximal end and said opposed end configured for connection to orthotic hardware secured to the lower portion of a body limb;
   a proximal bar associated with said housing so as to create a second axis of rotation and co-linear construction for rotation of said distal bar relative to said proximal bar, said proximal bar having an end configured for connection to orthotic hardware secured to the upper portion of a body limb;
   a snap ring positioned within said interior space of said housing, said snap ring having an interior surface and ratchet teeth associated with said interior surface;
   a brake wheel positioned within said interior space of said housing, said brake wheel having an exterior circumference that is configured as a pawl surface complementary to said ratchet teeth of said snap ring so as to provide one-direction movement of said brake wheel with incremental stops;
   a transfer gear positioned within said interior space of said housing, said transfer gear partially press-fit into said brake wheel to create a press-fit portion and an exposed portion and so that rotation of said brake wheel produces rotation of said transfer gear, said exposed portion of said transfer gear positioned to engage said large gear configuration integral to said proximal end of said distal bar, said transfer gear also sized relative to said large gear configuration to create a gear ratio reduction;
   an unlocking pin having a non-symmetrical perimeter configuration,
   a handle associated with said unlocking pin and configured for causing rotational movement of said unlocking pin; and
   a plurality of fasteners configured and positioned to secure said distal bar and said proximal bar relative to said housing in said co-linear construction, wherein once secured in their usable positions by said fasteners said snap ring, said brake wheel, and said transfer gear in combination produce a gear ratio reduction that allows a small stop increment for said distal bar during travel toward a position of maximum extension, and said handle rotated into an unlocked position where said snap ring around said brake wheel is held open by said unlocking pin which allows free rotation of said brake wheel, and corresponding free rotation of said distal bar relative to said proximal bar.

2. The mechanical joint of claim 1 wherein said gear ratio reduction allows stop increments of approximately three-degrees for said distal bar during travel toward a position of maximum extension.

3. The mechanical joint of claim 1 further comprising a stop pin configured and positioned to engage said large gear configuration integral to said proximal end of said distal bar so as to stop rotational movement of said distal bar at a position of maximum extension.

4. The mechanical joint of claim 3 wherein said stop pin allows said distal bar to travel approximately 135-degrees from a position of complete flexion to a position of full extension.

5. The mechanical joint of claim 1 wherein said proximal bar is a T-bar having a T-shaped proximal end and further wherein said housing has a complementary T-shaped recess sized to receive said T-shaped proximal end.

6. The mechanical joint of claim 1 wherein said fasteners comprise two pivot screws.

7. The mechanical joint of claim 1 further comprising a removable cover associated with said housing.

8. The mechanical joint of claim 7 wherein said fasteners secure said removable cover to said housing.

9. The mechanical joint of claim 7 wherein said fasteners comprise two pivot screws and said pivot screws are used to secure said removable cover to said housing.

10. A strong mechanical joint for use with orthotic hardware, said mechanical joint comprising:
- a housing with interior space;
- a removable cover associated with said housing;
- a distal bar associated with said housing so as to create a first axis of rotation, said distal bar having a proximal end and an opposed end, said distal bar also having a large gear configuration integral to said proximal end and said opposed end configured for connection to orthotic hardware secured to the lower portion of a body limb;
- a stop pin configured and positioned to engage said large gear configuration integral to said proximal end of said distal bar so as to stop rotational movement of said distal bar at a position of maximum extension;
- a proximal bar associated with said housing so as to create a second axis of rotation and co-linear construction for rotation of said distal bar relative to said proximal bar, said proximal bar having an end configured for connection to orthotic hardware secured to the upper portion of a body limb;
- a snap ring positioned within said interior space of said housing, said snap ring having an interior surface and ratchet teeth associated with said interior surface;
- a brake wheel positioned within said interior space of said housing, said brake wheel having an exterior circumference that is configured as a pawl surface complementary to said ratchet teeth of said snap ring so as to provide one-direction movement of said brake wheel with incremental stops;
- a transfer gear positioned within said interior space of said housing, said transfer gear partially press-fit into said brake wheel to create a press-fit portion and an exposed portion and so that rotation of said brake wheel produces rotation of said transfer gear, said exposed portion of said transfer gear positioned to engage said large gear configuration integral to said proximal end of said distal bar, said transfer gear also sized relative to said large gear configuration to create a gear ratio reduction;
- an unlocking pin having a non-symmetrical perimeter configuration,
- a handle associated with said unlocking pin and configured for causing rotational movement of said unlocking pin; and
- at least two fasteners configured and positioned to secure said distal bar and said proximal bar relative to said housing in said co-linear construction, wherein once secured in their usable positions by said fasteners said snap ring, said brake wheel, and said transfer gear in combination produce a gear ratio reduction that allows a small stop increment for said distal bar during travel toward a position of maximum extension, and said handle rotated into an unlocked position where said snap ring around said brake wheel is held open by said unlocking pin which allows free rotation of said brake wheel, and corresponding free rotation of said distal bar relative to said proximal bar.

11. The mechanical joint of claim 10 wherein said gear ratio reduction allows stop increments of approximately three-degrees for said distal bar during travel toward a position of maximum extension.

12. The mechanical joint of claim 10 wherein said stop pin allows said distal bar to travel approximately 135-degrees from a position of complete flexion to a position of full extension.

13. The mechanical joint of claim 10 wherein said proximal bar is a T-bar having a T-shaped proximal end and further wherein said housing has a complementary T-shaped recess sized to receive said T-shaped proximal end.

14. The mechanical joint of claim 13 wherein said fasteners comprise two pivot screws.

15. The mechanical joint of claim 14 wherein said fasteners comprise two pivot screws and said pivot screws are used to secure said removable cover to said housing.

16. The mechanical joint of claim 15 wherein said gear ratio reduction allows stop increments of approximately three-degrees for said distal bar during travel toward a position of maximum extension, and further wherein said stop pin allows said distal bar to travel approximately 135-degrees from a position of complete flexion to a position of full extension.

17. A strong mechanical joint for use with orthotic hardware, said mechanical joint comprising:
- a housing with interior space, said housing also having an exterior surface with a T-shaped recess;
- a distal bar associated with said housing so as to create a first axis of rotation, said distal bar having a proximal end and an opposed end, said distal bar also having a large gear configuration integral to said proximal end and said opposed end configured for connection to orthotic hardware secured to the lower portion of a body limb;
- a stop pin configured and positioned to engage said large gear configuration integral to said proximal end of said distal bar so as to stop rotational movement of said distal bar at a position of maximum extension;
- a T-bar associated with said housing so as to create a second axis of rotation and co-linear construction for rotation of said distal bar relative to said T-bar, said T-bar having a T-shaped proximal end with a configuration and dimension complementary to that of said T-shaped recess so that said T-shaped proximal end is able to be received within said T-shaped recess, said T-bar also having an opposed distal end configured for connection to orthotic hardware secured to the upper portion of a body limb;
- a snap ring positioned within said interior space of said housing, said snap ring having an interior surface and ratchet teeth associated with said interior surface;
- a brake wheel positioned within said interior space of said housing, said brake wheel having an exterior circumference that is configured as a pawl surface complementary to said ratchet teeth of said snap ring so as to provide one-direction movement of said brake wheel with incremental stops;
- a transfer gear positioned within said interior space of said housing, said transfer gear partially press-fit into said brake wheel to create a press-fit portion and an exposed portion and so that rotation of said brake wheel produces rotation of said transfer gear, said exposed portion of said transfer gear positioned to engage said large gear configuration integral to said proximal end of said distal bar, said transfer gear also sized relative to said large gear configuration to create a gear ratio reduction;
- an unlocking pin having a non-symmetrical perimeter configuration, a handle associated with said unlocking pin and configured for causing rotational movement of said unlocking pin; and at least two fasteners configured and positioned to secure said distal bar and said proximal bar relative to said housing in said co-linear construction, wherein once secured in their usable positions by said fasteners said snap ring, said brake wheel, and said transfer gear in combination produce a gear ratio reduction that allows a small stop increment for said distal bar during travel toward a position of maximum extension, and said handle rotated into an unlocked position where said snap ring around said brake wheel is held open by said unlocking pin which allows free rotation of said brake wheel, and corresponding free rotation of said distal bar relative to said proximal bar.

18. The mechanical joint of claim 17 wherein said gear ratio reduction allows stop increments of approximately three-degrees for said distal bar during travel toward a position of maximum extension.

19. The mechanical joint of claim 17 wherein said stop pin allows said distal bar to travel approximately 135-degrees from a position of complete flexion to a position of full extension.

* * * * *